(12) United States Patent
Goto et al.

(10) Patent No.: US 8,202,890 B2
(45) Date of Patent: Jun. 19, 2012

(54) PEST CONTROL AGENT

(75) Inventors: Kimihiko Goto, Yokohama (JP); Ryo Horikoshi, Yokohama (JP); Kazuhiko Oyama, Higashimurayama (JP); Satoshi Omura, Tokyo-To (JP); Toshiaki Sunazuka, Funabashi (JP)

(73) Assignees: Meiji Seika Pharma Co., Ltd., Tokyo To (JP); The Kitasato Institute, Tokyo To (JP)

( * ) Notice: Subject to any disclaimer, the term of this patent is extended or adjusted under 35 U.S.C. 154(b) by 385 days.

(21) Appl. No.: 12/312,866

(22) PCT Filed: Nov. 30, 2007

(86) PCT No.: PCT/JP2007/073161
§ 371 (c)(1),
(2), (4) Date: May 29, 2009

(87) PCT Pub. No.: WO2008/066153
PCT Pub. Date: Jun. 5, 2008

(65) Prior Publication Data
US 2011/0195998 A1 Aug. 11, 2011

(30) Foreign Application Priority Data
Nov. 30, 2006 (JP) ................................. 2006-324390

(51) Int. Cl.
*A01N 43/40* (2006.01)
*A61K 31/44* (2006.01)
*C07D 405/00* (2006.01)
(52) U.S. Cl. .................................... 514/338; 546/283.1
(58) Field of Classification Search .................. None
See application file for complete search history.

(56) References Cited

U.S. PATENT DOCUMENTS

| 7,491,738 B2 * | 2/2009 | Goto et al. .................... 514/338 |
| 2006/0281780 A1 | 12/2006 | Goto et al. |

FOREIGN PATENT DOCUMENTS

| JP | 4-360895 | 12/1992 |
| JP | 8-259569 | 10/1996 |
| JP | 8-269062 | 10/1996 |
| JP | 2006-513233 | 4/2006 |
| WO | 94/09417 | 4/1994 |
| WO | 2004/060065 | 7/2004 |
| WO | 2006/129714 | 12/2006 |

OTHER PUBLICATIONS

International Search Report dated Feb. 12, 2008 in the International (PCT) Application PCT/JP2007/073161 of which the present application is the U.S. National Stage.

Omura et al., "Pyripyropenes, Highly Potent Inhibitors of Acyl-CoA: Cholesterol Acyltransferase Produced by *Aspergillus fumigatus*", The Journal of Antibiotics, vol. 46, No. 7, pp. 1168-1169, 1993.
Toshiaki Sunazuka et al., "Synthetic Study of α-Pyrone Meroterpenoids, Pyripyropens", 有機合成化学協会誌, vol. 56, No. 6, pp. 478-488, 1998.
Hui-Juan Wang et al., "Aflavinines and Other Antiisectan Metabolites from the Ascostromata of *Eupenicillium crustaceum* and Related Species", Applied and Environmental Microbiology, vol. 61, No. 12, pp. 4429-4435, 1995.
Rika Obata et al., "Chemical Modification and Structure-activity Relationships of Pyripyropenes 3. Synthetic Conversion of Pyridine-pyrone Moiety", The Journal of Antibiotics, vol. 50, No. 3, pp. 229-236, Mar. 1997.
Rika Obata et al., "Chemical Modification and Structure-activity Relationships of Pyripyropenes 1. Modification at the Four Hydroxyl Groups", The Journal of Antibiotics, vol. 49, No. 11, pp. 1133-1148, Nov. 1996.
International Preliminary Report on Patentability and English translation of the Written Opinion issued Jun. 11, 2009 in corresponding International Application No. PCT/JP2007/073161.
Supplementary European Search Report dated Nov. 26, 2010 in corresponding European Application No. 07 84 9939.

* cited by examiner

*Primary Examiner* — Jeffrey Murray
(74) *Attorney, Agent, or Firm* — Wenderoth, Lind & Ponack, L.L.P.

(57) ABSTRACT

Disclosed is a compound usable as a pest control agent and has excellent pest control activity. A compound represented by formula (I) has excellent pest control activity. The compound or an agriculturally or horticulturally acceptable salt thereof is thus useful as a pest control agent.

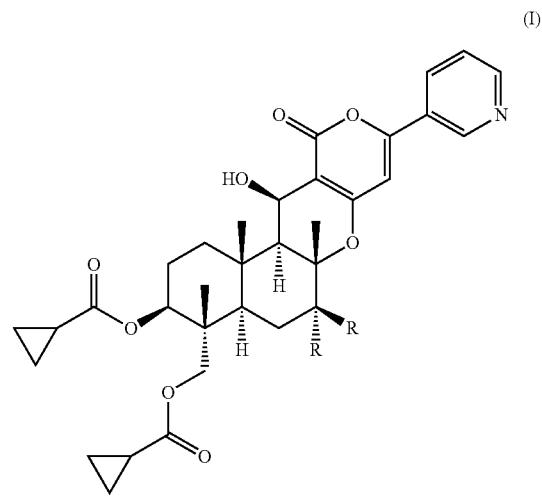

6 Claims, No Drawings

PEST CONTROL AGENT

BACKGROUND OF THE INVENTION

1. Field of Invention

The present invention relates to a novel Pyripyropene derivative and a composition for use as a pest control agent comprising the derivative as an active ingredient.

2. Background Art

Pyripyropene A has inhibitory activity against ACAT (acyl-CoA: cholesterol acyltransferase) and is expected to be applied, for example, to the treatment of diseases induced by cholesterol accumulation, as described in Japanese Patent Publication H04-360,895 A and Journal of Antibiotics (1993), 46 (7), 1168-9.

Further, pyripyropene analogues and derivatives and ACAT inhibitory activity thereof are described in Journal of Synthetic Organic Chemistry, Japan (1998), Vol. 56, No. 6, pp. 478-488, WO 94/09417, Japanese Patent Publication H08-259,569 A, and Japanese Patent Publication H08-269,062 A. These documents, however, do not disclose the compound which has a cyclopropylcarbonyloxy group at 1-, 7- or 11-position as a acyloxy group.

Furthermore, Applied and Environmental Microbiology (1995), 61 (12), 4429-35 describes that pyripyropene A has insecticidal activity against larvae of *Helicoverpa zea*. Furthermore, WO 2004/060065 describes that pyripyropene A has insecticidal activity against *Plutella xylostella* L larvae and *Tenebrio molitor* L. In these documents, however, there is no specific description on insecticidal activity of pyripyropene A against other pests.

Further, none of the above documents describes insecticidal activity of pyripyropene analogues and derivatives.

As far as the present inventors know, there is no document which discloses pyripyropene derivatives having cyclopropylcarbonyl group as mentioned above.

Up to now, many compounds having insecticidal activity have been reported and have been used as pest control agents. However, the presence of insect species, which are resistant to or can be hardly controlled by these compounds, has posed a problem. Accordingly, the development of a novel pest control agent having excellent insectidal activity has still been desired.

SUMMARY OF THE INVENTION

We have now found a novel pyripyropene derivative that has significant insecticidal activity. The present invention has been made based on such finding.

Accordingly, an object of the present invention is to provide a novel pyripyropene derivative that has significant insecticidal activity.

Accordingly, another object of the present invention is to provide a composition as a pest control agent which can reliably exhibit the contemplated effect and can be used safely and which comprises the novel pyripyropene derivatives or an agriculturally or horticulturally acceptable salt thereof and an agriculturally or horticulturally acceptable carrier.

The novel pyripyropene derivative according to the present invention is a compound represented by formula (I) or an agriculturally or horticulturally acceptable salt thereof.

[Chemical formula 1]

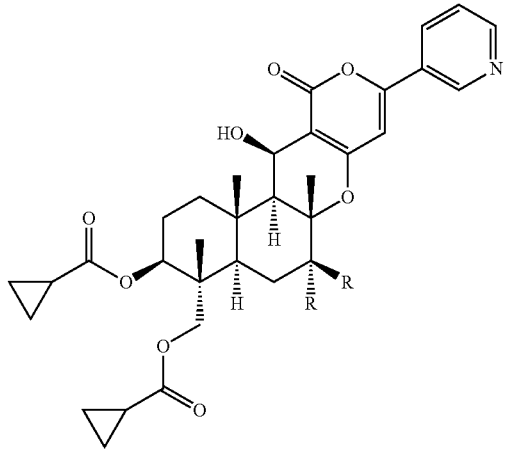

(I)

wherein two R's represent a hydrogen atom, respectively, or two R's may combine together to represent an oxo group.

Furthermore, a composition useable as a pest control agent according to the present invention comprises the novel pyripyropene derivatives represented by the formula (I) above or an agriculturally or horticulturally acceptable salt thereof and an agriculturally or horticulturally acceptable carrier.

Further, another object of the present invention is to provide a method for controlling a pest. The method according to the present invention, comprising applying an effective amount of the compound represented by formula (I) above or an agriculturally or horticulturally acceptable salt thereof to a plant or soil.

According to another aspect of the present invention, there is provided use of the compound represented by formula (I) above or an agriculturally or horticulturally acceptable salt thereof as a pest control agent.

DETAILED DESCRIPTION OF THE INVENTION

Agriculturally or horticulturally acceptable salts of the compounds represented by formula (I) include, for example, acid addition salts such as hydrochlorides, nitrates, sulfates, phosphates, or acetates.

The compounds represented by formula (I) can be synthesized from Pyripyropene A as a starting material by the method described in Japanese Patent Publication H08-259,569 A, Japanese Patent Publication H08-269,062 A, or Journal of Antibiotics (1997), 50 (3), pp. 229-36.

Pyripyropene A as a starting material is produced by the method described in Journal of Synthetic Organic Chemistry, Japan (1998), Vol. 56, No. 6, pp. 478-488 or WO 94/09417.

The compound represented by formula (I) according to the present invention has an excellent insecticidal activity to several insect species. Thus, according to the present invention, there is provided a composition useable as a pest control agent comprises the compound represented by the formula (I) above or an agriculturally or horticulturally acceptable salt thereof and an agriculturally or horticulturally acceptable carrier. The composition according to the present invention can be prepared by mixing the compound represented by the formula (I) above as an active ingredient with an agriculturally or horticulturally acceptable carrier.

Insect species against which the compound of formula (I) according to the present invention have control effect include: lepidopteran pests, for example, *Spodoptera litura, Mamestra brassicae, Pseudaletia separata*, green caterpillar, *Plutella xylostella, Spodoptera exigua, Chilo suppressalis, Cnaphalocrocis medinalis, Tortricidae, Carposimidae, Lyonetiidae, Lymantriidae*, pests belonging to the genus *Agrotis* spp., pests belonging to the genus *Helicoverpa* spp., and pests belonging to the genus *Heliothis* spp.; hemipteran pests, for example, *Aphidoidea* including *Aphididae, Adelgidae* and *Phylloxeridae* such as *Myzus persicae, Aphis gossypii, Aphis fabae, Aphis maidis* (corn-leaf aphid), *Acyrthosiphon pisum, Aulacorthum solani, Aphis craccivora, Macrosiphum euphorbiae, Macrosiphum avenae, Metopolophium dirhodum, Rhopalosiphum padi, Schizaphis graminum, Brevicoryne brassicae, Lipaphis erysimi, Aphis citricola*, Rosy apple aphid, *Eriosoma lanigerum, Toxoptera aurantii*, and *Toxoptera citricidus; Deltocephalidae* such as *Nephotettix cincticeps, Delphacidae* such as *Laodelphax striatellus, Nilaparvata lugens*, and *Sogatella furcifera; Pentatomidae* such as *Eysarcoris ventralis, Nezara viridula*, and *Trigonotylus coelestialium; Aleyrodidae* such as *Bemisia argentifolii, Bemisia tabaci*, and *Trialeurodes vaporariorum; Diaspididae, Margarodidae, Ortheziidae, Aclerdiae, Dactylopiidae, Kerridae, Pseudococcidae, Coccidae, Eriococcidae, Asterolecamidae, Beesonidae, Lecanodiaspididae*, or *Cerococcidae*, such as *Pseudococcus comstocki* and *Planococcus citri* Risso; *Coleoptera* pests, for example, *Lissorhoptrus oryzophilus, Callosobruchuys chienensis, Tenebrio molitor, Diabrotica virgifera virgifera, Diabrotica undecimpunctata howardi, Anomala cuprea, Anomala rufocuprea, Phyllotreta striolata, Aulacophora femoralis, Leptinotarsa decemlineata, Oulema oryzae, Carposimidae*, and *Cerambycidae; Acari*, for example, *Tetranychus urticae, Tetranychus kanzawai*, and *Panonychus citri; Hymenopteran* pests, for example, *Tenthredinidae; Orthopteran* pests, for example, *Acrididae; Dipteran* pests, for example, *Muscidae* and *Agromyzidae; Thysanopteran* pests, for example, *Thrips palmi* and *Frankliniella occidentalis*; Plant Parasitic Nematodes, for example, *Meloidogyne hapla, Pratylenchus* spp., *Aphelenchoides besseyi* and *Bursaphelenchus xylophilus*; and parasites of animals, for example, *Siphonaptera, Anoplura*, mites such as *Boophilus microplus, Haemaphysalis longicornis, Rhipicephalus sanguineus*, and *Scarcoptes scabiei*. Preferred are hemipteran pests.

hemipteran pests include *Aphidoidea* such as *Aphididae, Adelgidae*, and *Phylloxeridae*, particularly preferably *Aphididae; Pentatomidae*; and *Coccoidea* such as *Diaspididae, Margarodidae, Ortheziidae, Aclerdiae, Dactylopiidae, Kerridae, Pseudococcidae, Coccidae, Eriococcidae, Asterolecamidae, Beesonidae, Lecanodiaspididae*, and *Cerococcidae*. More preferred are *Myzus persicae, Aphis gossypii, Trigonotylus caelestialium* and *Pseudococcus comstocki*.

While the compound represented by formula (I) per se can be used as a pest control agent, the compound of the formula (I) can be prescribed in any suitable formulation, such as emulsifiable concentrates, EW formulations, liquid formulations, suspension, wettable powder, granulated wettable powder, dust, DL dust, dust granules, granules, tablets, oil solutions, aerosols, flowables, dry flowables, or micro-capsulated agents by using suitable carrier such as solid carriers, liquid carriers, gaseous carriers, surfactants, dispersants and/or other adjuvants for formulations, and the like.

Solid carriers usable herein include, for example, talc, bentonite, clay, kaolin, diatomaceous earth, vermiculite, white carbon, and calcium carbonate.

Examples of liquid carriers include: alcohols, such as methanol, n-hexanol, and ethylene glycol; ketones, such as acetone, methyl ethyl ketone, and cyclohexanone; aliphatic hydrocarbons, such as n-hexane, kerosine, and kerosene; aromatic hydrocarbons, such as toluene, xylene, and methylnaphthalene; ethers, such as diethyl ether, dioxane, and tetrahydrofuran; esters, such as ethyl acetate; nitriles, such as acetonitrile and isobutyronitrile; acid amides, such as dimethylformamide and dimethylacetamide; vegetable oils, such as soy bean oil and cotton seed oil; dimethylsulfoxide; and water.

Gaseous carriers include, for example, LPG, air, nitrogen, carbon dioxide, and dimethyl ether.

Surfactants or dispersants usable, for example, for emulsifying, dispersing, or spreading include, for example, alkylsulfonic esters, alkyl(aryl)sulfonic acid salts, polyoxyalkylene alkyl(aryl)ethers, polyhydric alcohol esters, and lignin sulfonic acid salts. Adjuvants usable for improving the properties of formulations include, for example, carboxymethylcellulose, gum arabic, polyethylene glycol, and calcium stearate.

The above carriers, surfactants, dispersants, and adjuvant may be used either solely or in combination according to need.

The content of the active ingredient in the formulation is not particularly limited. In general, however, the content of the active ingredient is 1 to 75% by weight for emulsifiable concentrates, 0.3 to 25% by weight for dust, 1 to 90% by weight for wettable powder, and 0.5 to 10% by weight for granules.

The compound represented by formula (I) or an agriculturally or horticulturally acceptable salt thereof and the above formulations comprising the same may be applied as such or after dilution to plants or soil. Therefore, according to another aspect of the present invention, there is provided a method for controlling pests comprising applying an effective amount of the compound represented by formula (I) above or an agriculturally or horticulturally acceptable salt thereof to a plant or soil.

Preferred methods usable for applying the compound or formulation to plants or soil include spreading treatment, soil treatment, surface treatment, and fumigation treatment. Spreading treatments include, for example, spreading, spraying, misting, atomizing, granule application, and submerged application. Soil treatments include, for example, soil affusion and soil mixing. Examples of surface treatments include, for example, coating, dust coating, and covering. Fumigation treatments include, for example, covering of soil with a plastic film after soil injection. Accordingly, the control method according to the present invention comprises a method in which the compound represented by formula (I) or a formulation comprising the same is applied by fumigation in a sealed space.

The composition as a pest controlling agent according to the present invention may be used as a mixture or in a combination with, for example, other insecticides, fungicides, miticides, herbicides, plant growth-regulating agents, or fertilizers. Agents which may be mixed or used in combination include those described, for example, in The Pesticide Manual, 13th edition, published by The British Crop Protection Council; and SHIBUYA INDEX, the 10th edition, 2005, published by SHIBUYA INDEX RESEARCH GROUP. More specifically, insecticides usable herein include, for example, organophosphate ester compounds such as acephate, dichlorvos, EPN, fenitrothion, fenamifos, prothiofos, profenofos, pyraclofos, chlorpyrifos-methyl, and diazinon; carbamate compounds such as methomyl, thiodicarb, aldicarb, oxamyl, propoxur, carbaryl, fenobucarb, ethiofencarb, fenothiocarb, pirimicarb, carbofuran, and benfuracarb; nereistoxin derivatives such as cartap and thiocyclam; organochlorine compounds such as dicofol and tetradifon; pyrethroid compounds such as permethrin, tefluthrin, cypermethrin, deltamethrin, cyhalothrin, fenvalerate, fluvalinate, ethofenprox, and silafluofen; benzoylurea compounds such as diflubenzuron, teflubenzuron, flufenoxuron, and chlorfluazuron; juvenile hormone-like compounds such as methoprene; and molting hormone-like compounds such as chromafenozide. Other compounds usable herein include buprofezin, hexythiazox, amitraz, chlordimeform, pyridaben, fenpyroximate, pyrimidifen, tebufenpyrad, fluacrypyrim, acequinocyl, cyflumetofen, flubendiamide, ethiprole, fipronil, ethoxazole, imidacloprid, chiothianidin, pymetrozine, bifenazate, spirodiclofen, spiromesifen, flonicamid, chlorfenapyr, pyriproxyfene, indoxacarb, pyridalyl, or spinosad, avermectin, milbemycin, organometallic compounds, dinitro compounds, organosulfur compounds, urea compounds, triazine compounds, hydrazine compounds. The composition according to the present invention may also be used as a mixture or in a combination with microbial pesticides such as BT formulations and entomopathogenic viral agents.

Fungicides usable herein include, for example, strobilurin compounds such as azoxystrobin, kresoxym-methyl, and trifloxystrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurace, benalaxyl, furalaxyl, and cyprofuram; sulfenic acid compounds such as dichiofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxylmide compounds such as procymidone, iprodione, and vinchlozolin; benzanilide compounds such as flutolanil and mepronil; morpholine compounds such as fenpropimorph and dimethomorph; organotin compounds such as fenthin hydroxide, and fenthin acetate; and cyanopyrrole compounds such as fludioxonil and fenpiclonil. Other compounds usable herein include fthalide, fluazinam, cymoxanil, triforine, pyrifenox, fenarimol, fenpropidin, pencycuron, cyazofamid, iprovalicarb, and benthiavalicarb-isopropyl and the like.

EXAMPLES

The present invention is further illustrated by the following Examples that are not intended as a limitation of the invention.

Synthesis Example 1

Compound 1

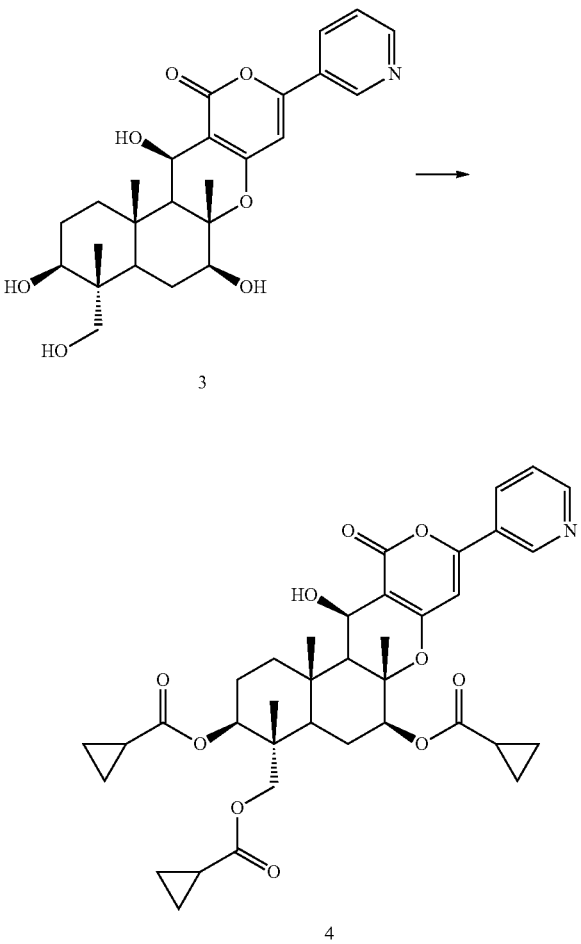

Compound 3 (1.12 g) synthesized by the method described in Japanese Patent Publication H08-259,569 A and cyclopropanecarboxylic acid (3.80 g) were dissolved in anhydrous N,N-dimethylformamide (10 ml), and 1-ethyl-3-(3-dimethylaminopropyl)-carbodiimide hydrochloride (4.70 g) and 4-(dimethylamino)pyridine (300 mg) were added to the solution. The reaction solution was stirred at room temperature for 5 hours and 10 minutes and was then poured into water, followed by extraction with ethyl acetate. The ethyl acetate layer was washed with saturated brine and was dried over anhydrous magnesium sulfate, and the solvent was removed by evaporation under the reduced pressure to give a crude product. The crude product was purified by chromatography on silica gel (Mega Bond Elut (Varian), acetone:hexane=1:1) to give compound 4 (1.54 g).

[Chemical formula 3]

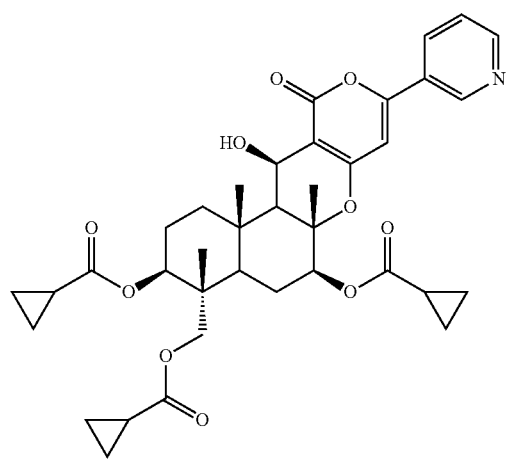

4

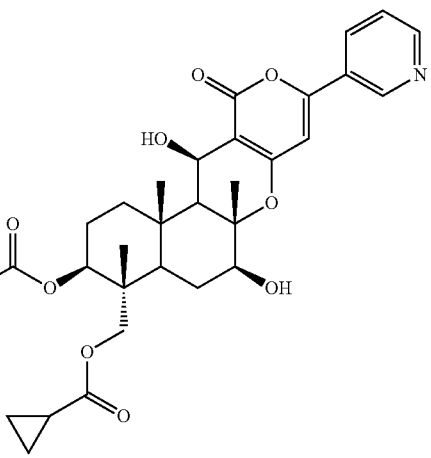

5

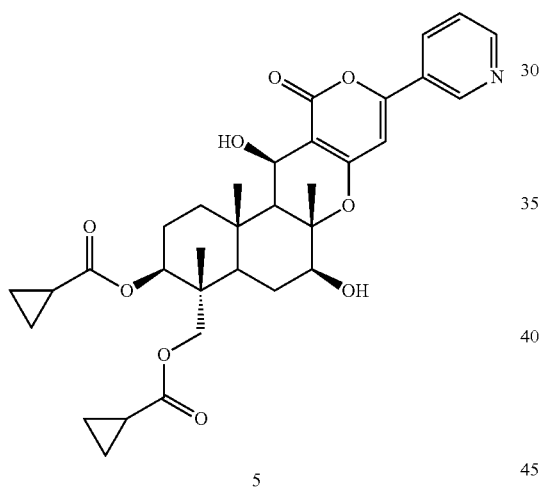

5

[Chemical formula 4]

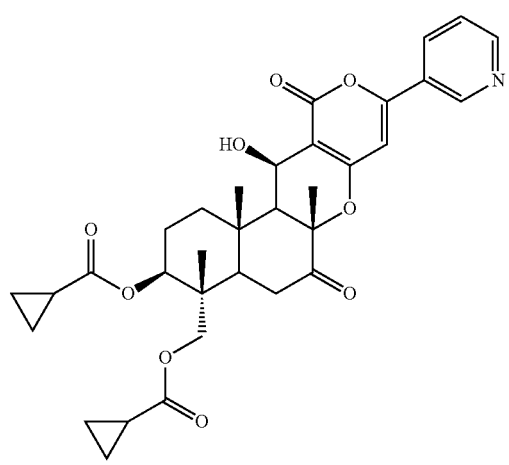

1

Compound 4 (1.07 g) was dissolved in an 80% aqueous methanol solution. 1,8-Diazabicyclo[5.4.0]-undeca-7-ene (271 mg) was added to the solution, and the mixture was stirred at room temperature for 24.5 hr. The reaction mixture was added with acetic acid to quench the reaction, and the solvent was removed by evaporation under the reduced pressure. Water was added to the precipitated crystal, followed by extraction with chloroform. The chloroform layer was washed with saturated brine and was dried over anhydrous magnesium sulfate, and the solvent was removed by evaporation under the reduced pressure to give a crude product of compound 5. The crude product was purified by chromatography on silica gel (Mega Bond Elut (Varian), acetone:hexane=1:1) to give compound 5 (233 mg).

Compound 5 (20 mg) was dissolved in dichloromethane (1 ml). Dess-Martin Periodinane (21 mg) was added to the solution at 0° C., and the mixture was stirred for 2 hours and 40 minutes. Saturated sodium thiosulfate solution was added into the solution, followed by extraction with chloroform. The chloroform layer was washed with saturated brine and was dried over anhydrous magnesium sulfate, and the solvent was removed by evaporation under the reduced pressure to give a crude product. The crude product was purified by preparative thin-layer chromatography (Merck Silica Gel 60 F 0.5 mm, acetone:hexane=1:1) to give compound 1 (5.4 mg).

Synthesis Example 2

Compound 2

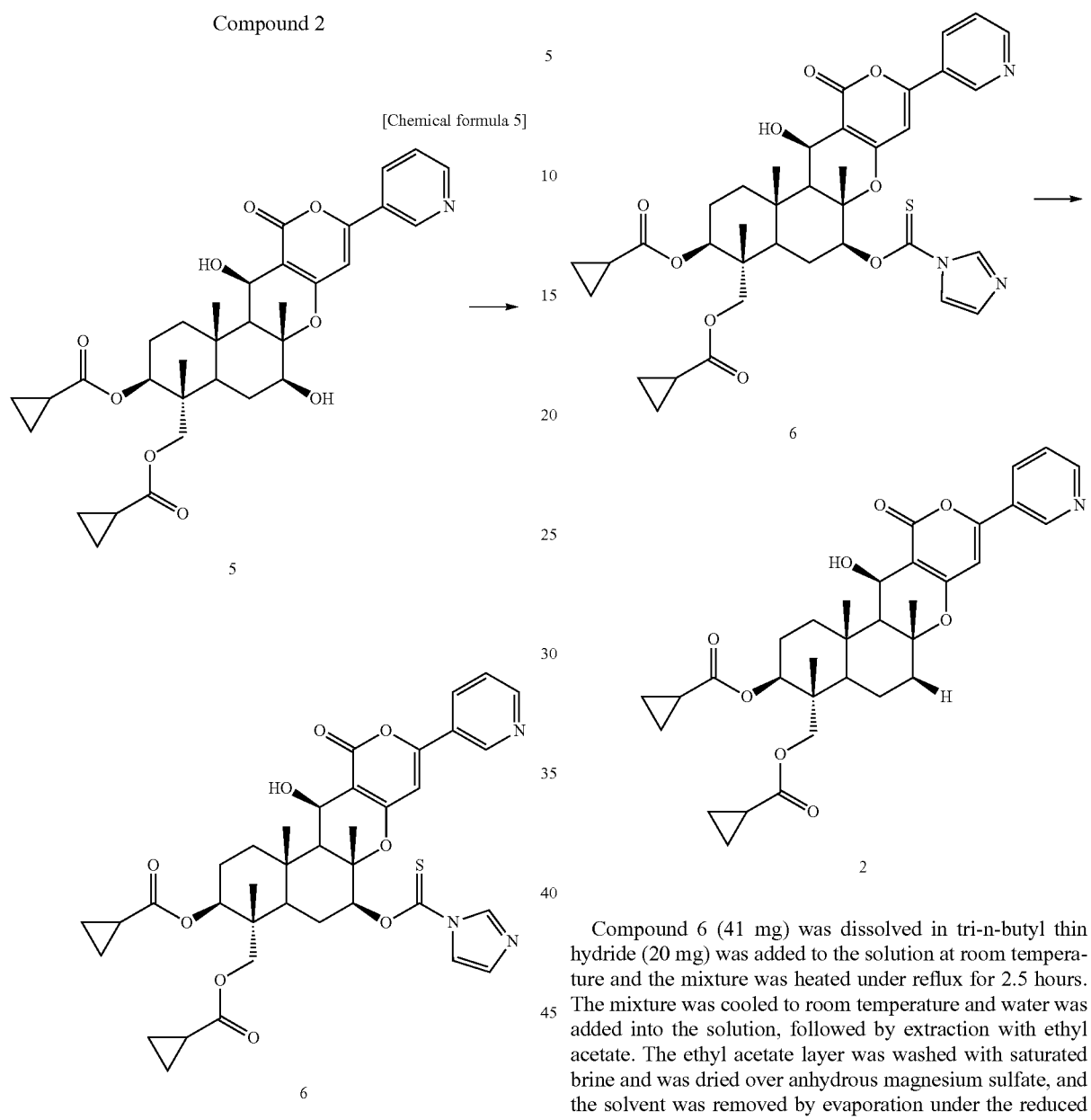

Compound 5 (50 mg) prepared in Synthesis Example 1 was dissolved in Toluene (3 ml). 1,1'-thiocarbonylimidazole (90 mg) was added to the solution at room temperature and the mixture was heated under reflux for 2.5 hours. The mixture was cooled to room temperature and water was added into the solution, followed by extraction with ethyl acetate. The ethyl acetate layer was washed with saturated brine and was dried over anhydrous magnesium sulfate, and the solvent was removed by evaporation under the reduced pressure to give a crude product. The crude product was purified by preparative thin-layer chromatography (Merck Silica Gel 60 F 0.5 mm, acetone:hexane=1:1) to give compound 6 (41.1 mg).

Compound 6 (41 mg) was dissolved in tri-n-butyl thin hydride (20 mg) was added to the solution at room temperature and the mixture was heated under reflux for 2.5 hours. The mixture was cooled to room temperature and water was added into the solution, followed by extraction with ethyl acetate. The ethyl acetate layer was washed with saturated brine and was dried over anhydrous magnesium sulfate, and the solvent was removed by evaporation under the reduced pressure to give a crude product. The crude product was purified by preparative thin-layer chromatography (Merck Silica Gel 60 F 0.5 mm, acetone:hexane=1:1) to give compound 2 (3.5 mg).

Table 1 below shows that $^1$H-NMR data and Mass spectrometric data of Compounds 1 and 2.

TABLE 1

| Compound No. | Solvent | NMR Data $^1$H—NMR δ (ppm) | Mass Analysis Method | Data |
|---|---|---|---|---|
| 1 | CDCl$_3$ | 0.83-1.00 (8H, m), 0.96 (3H, s), 1.44 (1H, m), 1.53-1.61 (2H, m), 1.63 (3H, s), 1.76 (1H, d, J=3.7 Hz), 1.81 (3H, s), 1.87 (2H, m), 1.94-1.97 (1H, m), | ESI | 592 (M + H)$^+$ |

TABLE 1-continued

| Com-pound No. | NMR Data Solvent | $^1$H—NMR δ (ppm) | Mass Analysis Method | Data |
|---|---|---|---|---|
| 2 | CDCl$_3$ | 2.21 (1H, m), 2.53 (1H, dd, J=2.6, 14.9 Hz), 2.78 (1H, t, J=14.9 Hz), 2.91 (1H, d, J=1.5 Hz), 3.66 (1H, d, J=12.0 Hz), 3.84 (1H, d, J=12.0 Hz), 4.82 (1H, dd, J=4.8, 11.7 Hz), 5.06 (1H, m), 6.71 (1H, s), 7.41 (1H, dd, J=4.8, 8.0 Hz), 8.09 (1H, dt, J=1.7, 8.0 Hz), 8.70 (1H, dd, J=1.7, 4.8 Hz), 9.02 (1H, d, J=1.7 Hz) 0.84-1.00 (8H, m), 0.90 (3H, s), 1.12-1.16 (1H, m), 1.25 (1H, s), 1.35-1.46 (1H, m), 1.41 (3H, s), 1.56-1.70 (5H, m), 1.66 (3H, s), 1.78-1.89 (2H, m), 2.12-2.17 (2H, m), 2.82 (1H, d, J=1.4 Hz), 3.69 (1H, d, J=11.9 Hz), 3.91 (1H, d, J=11.9 Hz), 4.83 (1H, dd, J=5.1, 11.5 Hz), 4.99 (1H, m), 6.46 (1H, s), 7.42 (1H, m), 8.11 (1H, dt, J=1.7, 8.0 Hz), 8.69 (1H, m), 9.01 (1H, m) | ESI | 578 (M + H)$^+$ |

Preparation Example 1

Wettable Powder

| | |
|---|---|
| Compound 1 | 30 wt % |
| Clay | 30 wt % |
| Diatomaceous earth | 35 wt % |
| Calcium lignin sulfonate | 4 wt % |
| Sodium laurylsulfate | 1 wt % |

The above ingredients were homogeneously mixed together, and the mixture was ground to prepare wettable powder.

Preparation Example 2

Dust

| | |
|---|---|
| Compound 1 | 2 wt % |
| Clay | 60 wt % |
| Talc | 37 wt % |
| Calcium stearate | 1 wt % |

The above ingredients were homogeneously mixed together to prepare dust.

Preparation Example 3

Emulsifiable Concentrate

| | |
|---|---|
| Compound 1 | 20 wt % |
| N,N-Dimethylformamide | 20 wt % |
| Solvesso 150 (Exxon Mobil Corporation) | 50 wt % |
| Polyoxyethylene alkylaryl ether | 10 wt % |

The above ingredients were homogeneously mixed and dissolved to prepare emulsifiable concentrate.

Preparation Example 4

Granules

| | |
|---|---|
| Compound 1 | 5 wt % |
| Bentonite | 40 wt % |
| Talc | 10 wt % |
| Clay | 43 wt % |
| Calcium lignin sulfonate | 2 wt % |

The above ingredients were homogeneously ground and homogeneously mixed together. Water was added to the mixture, followed by thorough kneading. Thereafter, the kneaded product was granulated and dried to prepare granules.

Preparation Example 5

Floables

| | |
|---|---|
| Compound 1 | 25 wt % |
| POE polystyrylphenyl ether sulfate | 5 wt % |
| Propylene glycol | 6 wt % |
| Bentonite | 1 wt % |
| 1% aqueous xanthan gum solution | 3 wt % |
| PRONAL EX-300 (Toho Chemical Industry Co., Ltd.) | 0.05 wt % |
| ADDAC 827 (K.I. Chemical Industry Co., Ltd.) | 0.02 wt % |
| Water | To 100 wt % |

All the above ingredients except for the 1% aqueous xanthan gum solution and a suitable amount of water were premixed together, and the mixture was then ground by a wet grinding mill. Thereafter, the 1% aqueous xanthan gum solution and the remaining water were added to the ground product to prepare 100 wt % floables.

Test Example 1

Pesticidal Effect Against *Myzus persicae*

A leaf disk having a diameter of 2.8 cmϕ was cut out from a cabbage grown in a pot and was placed in a 5.0 cm-Schale. Four adult aphids of *Myzus persicae* were released in the Schale. One day after the release of the adult aphids, the adult aphids were removed. The number of larvae at the first instar born in the leaf disk was adjusted to 10, and a test solution, which had been adjusted to a predetermined concentration by the addition of a 50% aqueous acetone solution (0.05% Tween 20 added) was spread over the cabbage leaf disk. The cabbage leaf disk was then air dried. Thereafter, the Schale was lidded and was allowed to stand in a temperature-controlled room (light period 16 hr-dark period 8 hr) (25° C.). Three days after the initiation of standing of the Schale, the larvae were observed for survival or death, and the death rate of larvae was calculated by the equation described later.

Test Example 2

Pesticidal Effect Against *Aphis gossypii*

A leaf disk having a diameter of 2.0 cmφ was cut out from a cucumber grown in a pot and was placed in a 5.0 cm-Schale. A test solution, which had been adjusted to a predetermined concentration by the addition of a 50% aqueous acetone solution (0.05% Tween 20 added) was spread over the cabbage leaf disk. After air dried, ten (10) of larvae of *Aphis gossypii* at the first instar were released in the Schale. Thereafter, the Schale was lidded and was allowed to stand in a temperature-controlled room (light period 16 hr-dark period 8 hr) (25° C.). Three days after the initiation of standing of the Schale, the larvae were observed for survival or death, and the death rate of larvae was calculated by the equation described later.

Test Example 3

Pesticidal Effect Against *Pseudococcus comstocki*

A leaf disk having a diameter of 2.8 cmφ was cut out from a leaf of *Phaseolus vulgaris* and was placed on an agar in a plastic cup, into which ten (10) of larvae of *Pseudococcus comstocki* at the first instar were released. A test solution, which had been adjusted to a predetermined concentration by the addition of a 50% aqueous acetone solution (0.05% Tween 20 added) was spread. After air dried, it was allowed to stand in a temperature-controlled room (light period 16 hr-dark period 8 hr) (25° C.). Three days after the initiation of standing of it, the larvae were observed for survival or death, and the death rate of larvae was calculated by the equation described later.

Results of Test Examples 1 to 3

The death rate of larvae was calculated by the following equation.

$$\text{Death rate (\%)} = \{\text{number of dead larvae}/(\text{number of survived larvae} + \text{number of dead larvae})\} \times 100$$

The concentrations which gave the death rate of 90% or more are shown in Table 2.

Comparative Tests

Compound PR-73 disclosed in Japanese Patent Publication H08-259,569 A and Compound PR-98 disclosed in Japanese Patent Publication H08-269,062 were also subject to the same tests described as Test Examples 1 to 3. The results are as shown in Table 2.

TABLE 2

Concentration (ppm) for the death rate of 90% or more

| Compound No. | Test Example 1 | Test Example 2 | Test Example 3 |
|---|---|---|---|
| 1 | 0.010 | 0.078 | 0.156 |
| 2 | 0.039 | 0.078 | 0.625 |
| PR-73 (comparative) | 5 | 5 | >20 |
| PR-98 (comparative) | 0.156 | 5 | >20 |

Test Example 4

Pesticidal Effect Against *Trigonotylus caelestialium*

A wheat seedling was immersed for 30 seconds in a solution, in which each test compound had been diluted to a predetermined concentration by the addition of a 50% aqueous acetone solution (Tween 20, 0.05% added). The wheat seedling was air dried, and then placed in a glass cylinder. Further, two larvae at the second instar of *Trigonotylus caelestialium* were released in the glass cylinder. The glass cylinder was then lidded, and the larvae were reared in the temperature-controlled room (25° C.). During the test, the wheat seedling was supplied with water from the bottom of the glass cylinder. Three days after the treatment, the larvae were observed for survival or death, and the death rate of the larvae was calculated by the following equation.

$$\text{Death rate (\%)} = \{\text{number of dead larvae}/(\text{number of survived larvae} + \text{number of dead larvae})\} \times 100$$

As a result, it was found that the death rate was not less than 80% for compound of Nos. 1 and 2 at a concentration of 100 ppm.

The invention claimed is:

1. A compound represented by formula (I) or an agriculturally or horticulturally acceptable salt thereof:

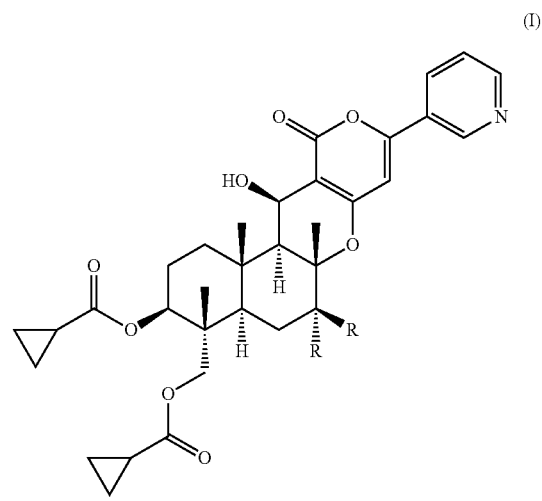

(I)

wherein the two R variables represent a hydrogen atom, respectively, or the two R variables may combine together to represent an oxo group.

2. A composition for use as a pest control agent, comprising a compound defined in claim 1 or an agriculturally or horticulturally acceptable salt thereof as an active ingredient and an agriculturally or horticulturally acceptable carrier.

3. A method for controlling a pest, comprising applying an effective amount of a compound represented by formula (I) defined in claim 1 or an agriculturally or horticulturally acceptable salt thereof to a plant or soil.

4. The method according to claim 3, wherein the pest is a hemipteran pest.

5. The method according to claim 4, wherein said hemipteran pest is selected from *Aphidoidea, Pentatomidae*, or *Coccoidea*.

6. The method according to claim 4, wherein the hemipteran pest is at least one pest selected from the group consisting of *Myzus persicae, Aphis gossypii, Trigonotylus caelestialium* and *Pseudococcus comstocki*.

* * * * *